(12) United States Patent
Palumbo et al.

(10) Patent No.: US 7,838,506 B2
(45) Date of Patent: Nov. 23, 2010

(54) DNA-BASED APTAMERS FOR HUMAN CATHEPSIN G

(75) Inventors: Manlio Palumbo, Padua (IT); Barbara Gatto, Padua (IT); Rodolfo Pescador, Milan (IT); Roberto Porta, Cernobbio (IT); Laura Iris Ferro, Milan (IT)

(73) Assignee: Gentium SpA, Villa Guardia (CO) (IT)

( * ) Notice: Subject to any disclaimer, the term of this patent is extended or adjusted under 35 U.S.C. 154(b) by 0 days.

(21) Appl. No.: 12/015,663

(22) Filed: Jan. 17, 2008

(65) Prior Publication Data

US 2008/0176814 A1    Jul. 24, 2008

Related U.S. Application Data

(63) Continuation of application No. 11/236,197, filed as application No. PCT/EP2004/006599 on Jun. 18, 2004, now abandoned.

(30) Foreign Application Priority Data

Jun. 30, 2003    (EP)    .................. 03425428

(51) Int. Cl.
  *A01N 43/04*    (2006.01)
  *A61K 31/70*    (2006.01)
(52) U.S. Cl. .................................... 514/44
(58) Field of Classification Search ............. 514/44
  See application file for complete search history.

(56) References Cited

U.S. PATENT DOCUMENTS 5,780,449 A * 7/1998 Bracht et al. ............ 514/44 R 6,316,190 B1    11/2001  Rein et al.
6,399,302 B1 *  6/2002  Lannigan et al. ............ 435/6
7,501,400 B1 *  3/2009  Tachas ..................... 514/44 R

FOREIGN PATENT DOCUMENTS

| EP | 0775745 A2 | 5/1997 |
| EP | 0775745 A3 | 10/1999 |
| WO | 9119813 A | 12/1991 |
| WO | 9214843 A1 | 9/1992 |

OTHER PUBLICATIONS

Vianini et al., "In vitro selection of DNA aptamers that bind L-tyrosinamide," Bioorganic & Medicinal chemistry, Oct. 2001, pp. 2543-2548, vol. 9, No. 10, Padova, Italy.
Bracht et al., "Isolation and functional characterization of a specific cathepsin G inhibitory aptamer from a pool of synthetic oligonucleotides," 1996, p. R13, Naunyn-Schmiedeberg's Archives of Pharmacoloty, vol. 353, No. 4.

* cited by examiner

*Primary Examiner*—Brian Whiteman
(74) *Attorney, Agent, or Firm*—Fredrikson & Byron, P.A.

(57) ABSTRACT

The present research is directed to the identification of non-peptidic inhibitors of cathepsin G characterised by high levels of selectivity and which can be efficaciously used in the treatment and prophylaxis of inflammatory occurrences and procoagulant conditions. The cathepsin G-inhibiting aptamers according to the invention consist of linear DNA or polynucleotide sequences having a chain length of at least 60 nucleotides and being substantially not subjected to undergo efficient base pairing.

11 Claims, 3 Drawing Sheets

Figure 1: Kd of the tested oligonucleotides.
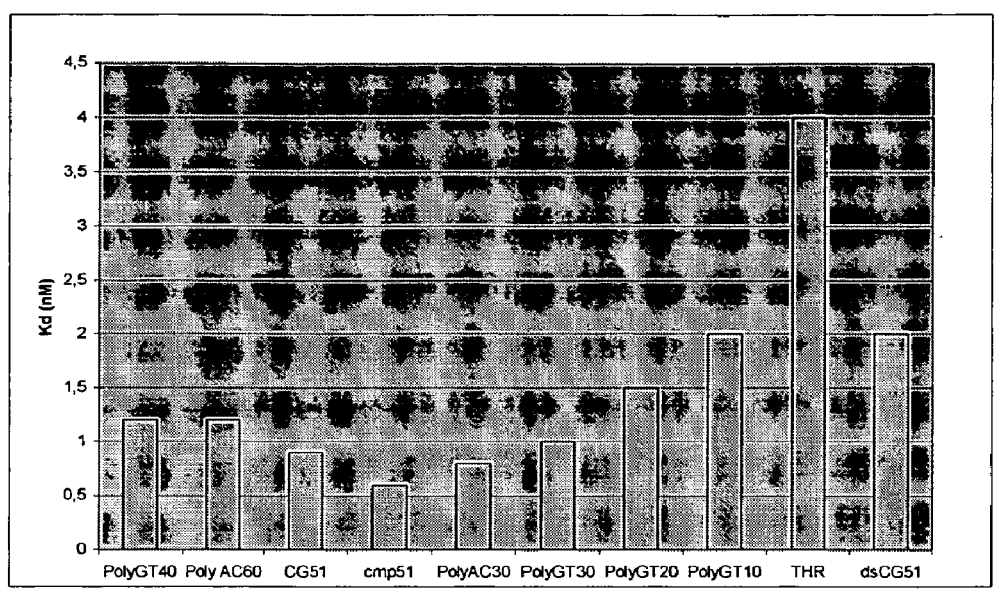

Figure 2. Concentration-Effect curves describing GT and AC aptamer binding to Cathepsin G from human neutrophils. GT 100 ( ▼ ), GT 80 ( ▽ ), GT 60 ( ■ ), AC 80 ( ◇ ), GT 40 ( □ ), AC 40 ( ▲ ), GT 30 ( ♦ ), GT 20 ( ● ), and AC 20 ( ○ ).
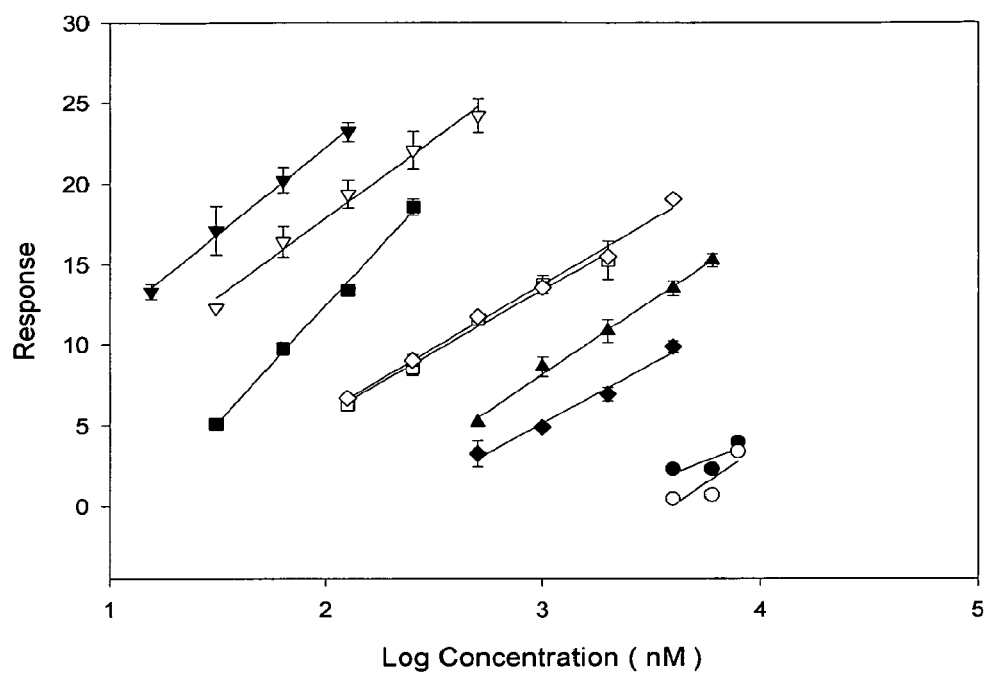

Figure 3 . Concentration-Effect curves describing PolyT aptamer binding to Cathepsin G from human neutrophils. PolyT100 ( o ), PolyT80 ( • ), PolyT60 ( ▼ ).
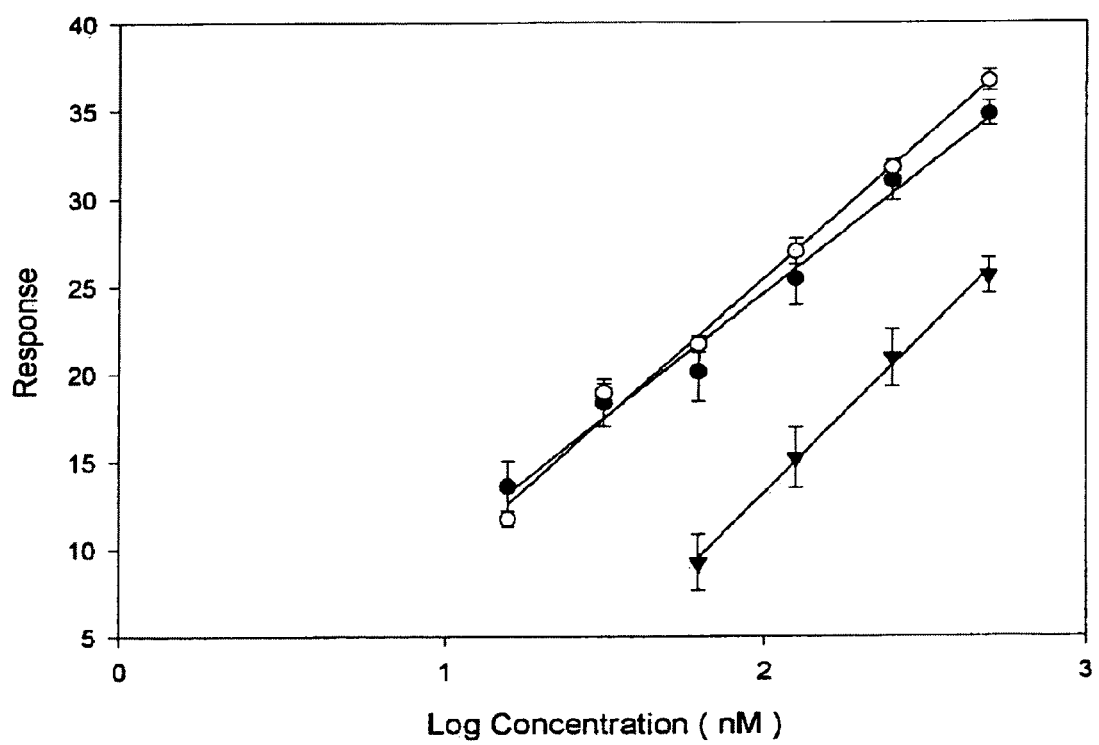

DNA-BASED APTAMERS FOR HUMAN CATHEPSIN G

RELATED APPLICATIONS

This application is a continuation of U.S. application Ser. No. 11/236,197, filed Sep. 27, 2005, now abandoned, which is a continuation of and claims priority to International Application No. PCT/EP2004/006599, filed Jun. 18, 2004, which in turn claims priority to European Application No. 03425428.4, filed Jun. 30, 2003, the teachings of all of which are incorporated herein by reference.

BACKGROUND OF THE INVENTION

Cathepsin G is a serine protease commonly found in the azurophilic granules of neutrophils and monocytes. Together with elastase and proteinase 3 it belongs to the chymotrypsin family and cleaves extracellular matrix proteins such as elastin, collagen, fibronectin and laminin causing extensive lung tissue damage in the animal.

Cathepsin G also plays a role in blood clotting; in fact, it is involved in an alternative pathway of leukocytes initiation of coagulation, and by activating coagulation factor X and factor V it can cleave and potentially modulate the thrombin receptor and it can activate platelets in vitro. It is also able to convert angiotensin I into angiotensin II with only minor cleavage occurring elsewhere in the molecule.

It was shown that cathepsin G kills bacteria and fungi but this property is not related to its activity, in fact peptides derived from its cleavage showed direct antimicrobial properties. It can also degrade necrotic tissues and is therefore related to several inflammatory diseases like lung emphysema, bronchitis, cystic fibrosis and psoriasis.

The enzymatic activity of cathepsin G is regulated by two types of protein proteinase inhibitors: the so called "canonical" inhibitors and the serpins. The former are relatively small proteins (29-190 amino acids) and are tight-binding reversible inhibitors; among them are Mucus proteinase inhibitor (MPI), eglin c and aprotinin. Serpins are larger proteins (400-450 residues) that form an irreversible complex with their cognate protein due to the formation of a non-hydrolysable acyl bond between the catalytic site of cathepsin G and their reactive site loop. Among serpins 1-antichymotrypsin is the most important: inhibitors of this family are not selective because they are able to bind to and inhibit other chymotripsins. Moreover, their stability and distribution in vivo is affected by their peptidic nature.

Several synthetic inhibitors were found starting from peptidomimetic scaffolds containing 1,2,5-thiadiazolidin-3-one 1,1 dioxide or 1,3-diazetidine-2,4-diones and some of them (particularly those with aromatic side chains) showed a remarkably specific activity for cathepsin G. However, they form non-reversible acyl complexes with the enzyme.

Recently, it was shown that both the full length and cleaved chromosomal DNA is able to bind and inhibit Cathepsin G in vitro and in vivo. A 30 bpDNA fragment tightly binds cathepsin G at physiological conditions and showed a decreasing order of affinity for human neutrophil elastase when compared to proteinase 3 in accordance with their decreasing cationic character.

In particular, EP-775745 discloses oligonucleotide cathepsin G-inhibiting aptamers having a chain length of about 40 nucleotides (and in any case lower than 55 nucleotides) and containing G-pairs repeating units which are useful in the treatment and prophylaxis of inflammatory occurrences and procoagulant conditions.

BRIEF DESCRIPTION OF THE DRAWINGS

FIG. 1 represents a comparison of the Kd of the tested oligonucleotides.

FIG. 2 represents a summarization of the Log concentration-effect curves of GT and AC aptamers.

FIG. 3 represents a summarization of the Log concentration-effect curves of PolyT aptamers.

DESCRIPTION THE INVENTION

The present research is mainly directed to the identification of non-peptidic inhibitors of cathepsin G characterised by high levels of selectivity and which can be thus more efficaciously used in the treatment and prophylaxis of the above conditions and also in that of genetic diseases, degenerative diseases, DNA damages, neoplasia and/or skin diseases.

Like antibodies, DNA molecules are able to assume a variety of tridimensional structures depending on their sequence. Some of these might be relevant for binding to the target. In the present study we applied a method called SELEX (Systematic evolution of ligands by exponential enrichment) to select and identify ssDNA or RNA molecules, called aptamers, exhibiting high affinity for cathepsin G.

Aptamer technology combines the capacity of generating huge structural diversity in random pools of oligonucleotides with the power of the polymerase chain reaction (PCR) to amplify selected sequences. This technology involves the screening of large, random-sequence pool of oligonucleotides and is based on the fact that they assume a large number of tertiary structures, some of which may possess desirable binding or catalytic activity against target molecules.

Although inhibition is not demanded by the selection, in many cases these ligands directly inhibit the biological functions of the targeted proteins. In these cases, the inhibitory functions of the ligands are presumably due to overlapping of their binding sites with the functional region of proteins.

The outcome of our research has lead us to define a new class of cathepsin G-inhibiting aptamers possessing particularly high levels of selectivity. The new cathepsin G-inhibiting aptamers of the present invention are single or double stranded linear DNA or polynucleotide sequences characterized by having a chain length of at least 60 nucleotides, preferably 70, and by being substantially not subjected to inter and/or intra molecular base pairing.

According to the best embodiment of the invention the DNA sequences may have a chain length of 70-120 nucleotides, preferably of 70-110 nucleotides, even more preferably of 80-100 nucleotides. Although the sequences according to the present invention may be single or double stranded, single stranded sequences are preferred. The sequences according to the present invention are also preferably characterized by having a molar content in guanine of about 25-50%, preferably 35-45% and/or by having a molar ratio AG/TC of about 1.0÷2.0, preferably 1.2÷1.8 (for the purposes of the present invention AG means the total number of A and G nucleotides of the sequence whereas TC means the total number of T and C nucleotides of the sequence).

Preferred embodiments of the invention are:

$(GT)_n$ or $(AC)_n$ oligopolymers in which n is in the range from 35 to 60, preferably from 40 to 50;

$(T)_n$ or $(G)_n$ or $(A)_n$ or $(C)_n$ or $(Inosine)_n$ omopolymers in which n is in the range from 70 to 120, preferably from 80 to 100.

Within the terms of the present invention the expression "substantially not subjected to inter and/or intra molecular base pairing" means that the DNA or polynucleotide sequences do not undergo inter and/or intra molecular base pairing to an extent higher than 20%, preferably than 10%, even more preferably than 5%, under both stringent and non stringent conditions. Such a result is the direct consequence of their structure, since the fact of:

having a molar ratio AG/TC of 1.0÷2.0; or being $(GT)_n$ or $(AC)_n$ oligopolymers in which n is higher than 30; or being $(T)_n$ or $(G)_n$ or $(A)_n$ or $(C)_n$ or $(Inosine)_n$ omopolymers in which n is higher than 60;

de facto prevents any sort of hybridization.

As it will be apparent from the following discussion, the aptamers according to the present invention do selectively and efficaciously inhibit cathepsin G and, consequently, they can be used in the manufacture of a medicament for the treatment and prophylaxis of inflammatory occurrences, pro-coagulant conditions, genetic diseases, degenerative diseases, DNA damages, neoplasia and/or skin diseases, which represents therefore an object of the invention. A further object of the invention is also represented by the pharmaceutical composition containing the cathepsin G-inhibiting aptamers of the invention together with customary excipients and/or adjuvants. Other objects of the invention may be represented by the cathepsin G-inhibiting aptamers selected from those reported in the sequence listing (i.e. from SEQ ID NO: 1 to SEQ ID NO: 18).

EXPERIMENTAL SECTION

Materials

Cathepsin G was purchased from Europa Bioproducts or from Calbiochem. All oligonucleotides were obtained from Eurogentec Bel SA (Belgium) and purified by PAGE before use. Some oligonucleotides, already purified by PAGE were obtained from Gibco BRL Custom Primers. Taq polymerase was from Pharmacia Amersham Biotech while dNTPs were purchased as sodium salt from Boehringer Mannheim.T4-polynucleotide kinase, ligase and the restriction enzymes were from Gibco Life Technologies. Qiagen kits were used for plasmid miniprep purification, and sequencing was performed using T7 Sequenase (Pharmacia Amersham Biotech) and [gamma-$^{33}$P]dATP (Nen Life Sciences).

ssDNA Library

The synthesised random pool is 96 base length, the central part of the molecule has a randomised region that is flanked by two constant regions for amplification, cloning and sequencing; its sequence is 5'-CGTACGGAATTCGCTAGC(N)$_{60}$GGATCCGAGCTCCACGTG-3' (Referred to herein as SEQ ID NO: 19). The underlined sequences refer to restriction sites for EcoRI and BamHI enzymes respectively.

The pool was amplified by PCR using primer II-up, which sequence is 5'-CGTACGGAATTCGCTAGC-3', and primer III-Down 5'Biot-CACGTCGAGCTCGGATCC-3' (Referred to herein as SEQ ID NO: 20) which is biotinylated at the 5' end in order to be bound to a streptavidin column to get ssDNA.

Selection Protocol

The starting random pool was radioactive labelled with $^{32}$P, denaturated at high temperature and incubated with cathepsin G in Incubation buffer (buffer IB: 30 mM Tris HCl pH7.5, 150 mM NaCl, 5 mM KCl and 5 mM MgCl$_2$) which is close to the physiological conditions.

The incubation was conducted for 90 minutes in ice, then the sample was loaded in an affinity chromatography mini-column filled with Sepharose SP (Amersham Pharmacia Biotech), swollen and equilibrated in buffer IB. The ssDNA/ protein solution was incubated with the resin for 30 minutes at 4° C. The unbound oligonucleotide molecules were washed away with buffer IB, while the remaining, more selective ones were eluted from the column a high ionic force elution buffer (buffer EB: 0.8 M NaCl e 50 mM Tris pH 7.8).

The washing volumes were modified during the selection in order to increase the stringency as well as the DNA concentration which was twice the protein at the first cycle, but it was progressively reduced.

The fractions were counted and the yield of the Selex cycle was expressed as a percentage of the total radioactivity. The flow through and the first two fractions of the EB wash were collected and amplified.

Polymerase Chain Reaction

Polymerase chain reaction was done using Taq polymerase at a concentration of 0.3-0.5 u/50 µl in the buffer indicated by the producer. The number of cycles was adjusted after every different selection.

Before the insertion in the plasmid vector for cloning, the DNA was subjected to a polishing reaction in order to get blunt ends: an aliquot of the normal PCR reaction was incubated with 2.5 u/µl of Pfu Turbo polymerase (Stratagene) in the suggested buffer at 72° C. for 30 minutes.

Generation of ssDNA

In order to get ssDNA from the amplified dsDNA we used alkaline denaturation protocol. The DNA was amplified using a biotinilated Down-II primer and bound to a chromatography column filled with streptavidin Sepharose (Pierce). After 30 minutes incubation the unbound dsDNA was washed away with buffer NaCl 50 mM, Tris/HCl 100 mM, EDTA 10 mM (SBB-strepavidin Binding Buffer) while the remaining one was denaturated and washed with NaOH 0.15 N. Then it was precipitated and collected for the selection cycles.

Cloning and Sequencing

Both the amplified dsDNA and the vector pUC19 (Amersham-Pharmacia Biotech) were treated with 2.5 units of EcoRI while only the plasmid was treated with SmaI that gives blunt ends.

After precipitation 3 pmols of dsDNA and 0.6 pmols of pUC19 were reacted with T4 ligase in the suggested buffer.

The plasmid was then inoculated in *E. coli* competent cells (SURE strain Stratagene) by the electroporation method using *E. coli* pulser (Biorad) and plated in solid LB media in the presence of Ampicillin, X-Gal and IPTG (for the blue/white screening). 50 white different colonies were picked, grown and harvested separately in liquid LB broth. Plasmids were purified by alkaline lysis and their quality was every time tested by agarose gel electrophoresis.

The sequence of the aptamers was determined with the Sanger's method, labeling with [gamma-$^{33}$P]dATP and employing two different primers EleA457: 5'-ACG-CCA-AGC-TTG-CAT-3' (Referred to herein as SEQ ID NO: 21) (sense) and Ele S: 5'-GGG-TTT-TCC-CAG-TCA-CGA-3' (Referred to herein as SEQ ID NO: 22) (antisense).

Kd and Ki Determination

The affinity of the oligonucleotides was determined by affinity chromatography as performed in the selection. Different aliquots of each oligonucleotide were previously incubated with 15 µg of Cathepsin G in ice. The solution was then loaded in the min-chromatography column used for the selection and washed with 15 volumes of buffer IB. After one hour incubation, it was washed with six volumes of buffer EB. Fractions of the same volumes were collected and counted.

Surface Plasmon Resonance (SPR) Experiments

Cathepsin G, from human neutrophils, dissolved in HBS EP buffer, pH 7.40 (Biacore) was immobilized on the surface of a CM 5 research grade sensor chip flow cell, according to the procedure suggested by Biacore and using the Biacore amine coupling kit. A blank flow cell was prepared using all the above reagents but Cathepsin G. The amount of Cathepsin G immobilized on the surface of the flow cell was 5178.91±129.63 RU.

Aptamers [Poly GT (chain length: 20, 30, 40, 60, 80 and 100) and Poly AC (chain length: 20, 40 and 80,] were dissolved in 30 mM Tris-HCl buffer, pH 7.50, 150 mM NaCl, 5 mM KCl, and 5 mM MgCl 2 and injected over the Cathepsin G surface or the blank surface. Three sets of experiments were run. The first at a concentration of 500 nM, for all the aptamers, the second at a concentration of 6595 µg/L, for all the aptamers, and the third one at concentrations ranging from 15.6 to 8000 nM, according to the aptamer being tested. All the above experiments were run at 25° C., using as running buffer the Biacore HBS EP Buffer, pH 7.40 The Cathepsin G surface was regenerated by two injections of 2 M NaCl. The blank sensorgram was subtracted from each sample sensorgram and the binding response evaluated. The binding responses, generated in the third set of experiments, were plotted as a function of the Log concentration (nM) to get concentration-effect curves to find out the relative potencies of aptamers in binding Cathepsin G from human neutophils.

RESULTS

Selection and Identification of Aptamers

We selected aptamers for cathepsin G starting from a DNA pool with a randomised region of 60 nucleotides flanked by two regions with conserved sequence for the PCR reaction and restriction sites for the following cloning step (see above).

We chose affinity chromatography as selection method, binding the protein to the resin. This appeared to be the easiest protocol because cathepsin G, which is positively charged at physiologic conditions (theoretical isoelectric point 11), can be tightly bound to an ion exchange resin, while an unspecific binding of the DNA molecules to the resin is highly reduced. In fact only the DNA molecules that recognise the protein remain on the column while the unbound material is washed away. We tried to render the binding process between the labelled ssDNA and the protein more selective by including potassium and magnesium chloride 5 mM in the binding buffer thus increasing ionic strength in the buffer and stabilising oligonucleotide folding.

The selected molecules were then efficiently removed from the column, together with the bound protein, using a high ionic strength buffer (buffer EB), and then counted by radioactivity. The first two fractions and the flow through were then collected, amplified by PCR and reduced to single stranded molecules in order to be used for the next cycle (see methods section for details).

We performed nine cycles of selection: after four cycles a significant increase of yield was observed, but the SELEX was terminated when no further increase in pool affinity was observed over three rounds, reaching a final yield of 42% (table 1). The stringency of the selection was increased changing the number and the volumes of the washes. After cycles 5 and 7 precolumn cycles were performed in order to avoid an unspecific binding of the aptamers to the resin: the pool coming from the previous cycle were loaded in the column without the protein: the first fractions eluted from the column were then amplified and used for the next cycle.

TABLE 1 scheme of the SELEX cycles.

| Cycle number | Protein µg | Column Volume (µg) | Wash Fraction | Cycle Yield % |
|---|---|---|---|---|
| 1 | 100 | 2000 | 8 × 1000 µl | 0.4 |
| 2 | 50 | 500 | 8 × 500 µl | 0.7 |
| 3 | 50 | 400 | 8 × 600 µl | 1.6 |
| 4 | 50 | 400 | 8 × 500 µl | 38 |
| 5 | 40 | 1000 | 9 × 1000 µl | 22 |
| precolumn | | 1000 | 10 × 250 µl | |
| 6 | 33 | 1000 | 20 × 250 µl | 22 |
| 7 | 30 | 500 | 23 × 500 µl | 21 |
| precolumn | | 300 | 10 × 200 µl | |
| 8 | 30 | 500 | 22 × 500 µl | 31 |
| 9 | 30 | 500 | 25 × 500 µl | 42 |

Sequence Analysis

The selected molecules were cloned into E. coli cells as described in the experimental section and sequenced. We found 19 different sequences out of 50 clones. We used two sequence alignment programs, Clustal W and FastA-align, searching for a repeated consensus motif, but the molecule diversity was too high to yield a good alignment even within subsets of the sequenced molecules. Further analysis showed that GT motifs are clearly repeated in 14 sequences. Moreover, a closer look at these molecules showed that they are not prone to undergo either inter and intra molecular base pairing to an appreciable extent, nor do they form more complex tridimensional structures like G quartets. It seemed that the selection led to unstructured, linear and flexible molecules that can tightly bind to the positive protein because of a charge-charge interaction. To confirm this hypothesis, we compared the affinity of one of the selected aptamers, the 60mer CG51, with other oligonucleotides having non-pairing sequences such as oligo GT or AC structures. The sequences of the oligonucleotides coming from the last selection cycle are reported here-below; each one is marked with a different number (CG51 and CG43 are the same).

CG1
GGGTGGCCCCCTAGTCGCGCACTGGAAGCGGTAGTGTCGTGAGATTCGTA
TCTGGGGTAT

CG3
CAACGAGTCAGGGCGTGATTGGTGAAGATGTGTGGTTTGGCCAGAAAGGG
CGATGGTGGA

CG11
AGAGCTGAGACGGACATGCTGCCCATGGAGACTGTTCGAGAGGGTGAGCG
GGAGTGGG

CG16
ACCCCTAGGTCAGCACGTAGTGTAGGGCGATGTGTTCATGGCGGGAATGT
GAGTTGTGGG

CG20
GGGCGGCTCGCGTTGTGGAACATTCGTGGTGCCAATGCGTACCAGGGATT
GCCTCCTGT

CG25
GGGCGATTGGCGAATGCAAGGGTAAGGTTGGGCGATTGATGTGCACGTAG
CGCAGAGCAT

-continued

CG28
GGAACGTGGTAGGTGTGTCTGCTGTGTGTGGCTCGGGCAGGTTGTCAGGG

TGTTT

CG32
GGGCATAGGGCGTCGTAGCCTGAAGGTGTGATTCGTGCGTTAGATGGGGG

GCAGTCTGC

CG39
CGGTGGAGAGGTCGCAATGACACGGTTGACGATAGGCCCCTTGCTAACAT

CGGTTGGTG

CG43
CAACGTGTGATATGTGGGTATACGCTTGGGTGTTACGCTGAGCACAGAGG

GTATTCGTGT

CG48
AGSGGGCAGCAGCACACCACACATGTACGTGGGGGATTGCATTGTGTACT

TAGACGGTAT

CG49
GGCCTGGGTGATGTACTATGTATGCGTCGTGGTGGCTGGTAAAGGGGTC

TGCTATGGGT

CG51
CAACGTGTGATATGTGGGTATACGCTTGGGTGTTACGCTGAGCACAGAGG

GTATTCGTGT

CG2
CCACGGACGCTGTGAGCGGCCAACGGATGGGAATCACGATCTGGCCCGAA

CCACATACCG

CG31
TCACACTAGGGCACTTGCTAAGTAGCTATGTAACTCGATCATACTTATTA

GGCTTG

CG23
AATCGATGGACACTTCAACGCAACTTGACATGGCGGTACGTGGACTCTTG

TGGCGACAGTT

CG34
AACCCGTGTGATAAGGATATGGTGACTTCGTGGCACAGCGTCGACGGACT

GCCCATTCCA

CG45
GGCGGGCGGTATGGGCTGCAGGATATGCAGGGGCGCAGAGGACAGTCTGG

CCATGTACTA

CG40
GGCAGGGACGTTCCCAGGAATGCGGCACAGGCAGACAGCTCCCGACGAGT

ACCAGGGTG

The above sequences have the following correspondence in the sequence listing:

CG1=SEQ ID NO: 1, CG3=SEQ ID NO: 2, CG11=SEQ ID NO: 3, CG16=SEQ ID NO: 4, CG20=SEQ ID NO: 5, CG25=SEQ ID NO: 6, CG28=SEQ ID NO: 7, CG32=SEQ ID NO: 8, CG39=SEQ ID NO: 9, CG43 (and CG51)=SEQ ID NO: 10, CG48=SEQ ID NO: 11, CG49=SEQ ID NO: 12, CG2=SEQ ID NO: 13, CG31=SEQ ID NO: 14, CG23=SEQ ID NO: 15, CG34=SEQ ID NO: 16, CG45=SEQ ID NO: 17, CG40=SEQ ID NO: 18.

Affinity of Selected Molecules and Related Sequences to Cathepsin G

We evaluated the oligonucleotide binding to cathepsin G by affinity chromatography in analogy with the selection method. The affinity of the aptamer CG51 was firstly compared with AC and GT oligonucleotides of the same length that, as mentioned, are clearly unable to fold into any structure characterised by Watson-Crick base pairs or G quartets formation. The complementary sequence of CG51, called cmpCG51, was included as a control. Moreover, in order to demonstrate whether the oligonucleotide length was an important factor in the binding to the protein, the affinity of AC and GT oligonucleotides longer and shorter than 60 nucleotides was measured.

As expected from the high yield of the SELEX, the selected CG51 showed a high affinity for cathepsin G (Kd 0.9 nM). Besides, its Kd was comparable with AC and GT oligonucleotides of the same length (Kd 0.8 nM and 1 nM respectively) and with cmpCG51 (Kd 0.6 nM) (FIG. 1). These data indicate that our hypothesis about tight binding by unstructured and flexible molecules was correct.

Molecules longer than the 60mer like $(AC)_{60}$ and $(GT)_{40}$, which are respectively a 120mer and a 80mer, showed an affinity of 1.2 nM. On the other hand, the shorter $(GT)_{20}$ and $(GT)_{10}$ that are shorter molecules, have a Kd of 1.5 nM and 2 nM respectively, suggesting that the length of the selected oligonucleotides is important to grant efficient binding.

Aptamer THR, that was selected against thrombin, was also included as a control in order to prove whether the oligonucleotide structure was important for cathepsin binding. This aptamer is known to form stable G quartets. The low Kd (4 nM) found in this case shows that this type of structure is not likely to represent an effective recognition motif.

Interestingly, double stranded CG51 showed an affinity lower than the single stranded, even if the latter bears a larger number of charged groups. Indeed, the double stranded oligonucleotide is bulkier and stiffer, hence unable to optimally bind the protein.

Surface Plasmon Resonance (SPR) Experiments

The data generated in the first set of experiments (each aptamer at 500 nM) gave the first evidence that, in the instance of GT aptamers, increasing the chain length over 60 brings forth an increase in binding but this increase is less steep than that in the range 30-60. The binding is poor in the range 20-30. In the instance of AC aptamers, their binding was less pronounced than that of GT aptamers. SPR resonse is related to the change in surface mass concentration of analyte (in the present instance aptamer) and therefore it depends on the molecular weight of the analyte in relation to the number of binding sites on the surface (made of Cathepsin G, in the present instance). To get rid of the doubt that the apparent aptamer binding was not dependent on the aptamer mass but just on the aptamer structural feature, a second set of experiments was carried out at the same mass concentration (each aptamer at 6595 µg/L). The results were the same as those obtained in the first set of experiments (data not shown for the sake of brevity). In FIG. 2, the Log concentration-effect curves of GT and AC aptamers are summarized. In this figure, just each aptamer responses, referring to the concentration range over which a linear regression was obtained, are reported. GT 100 is the most potent aptamer and it has been arbitrarily assigned a potency of one (the relative standard). GT 80 has a relative potency of about 0.32, GT 60 of about 0.144, AC 80 of about 0.017, GT40 of about 0.016, AC 40 of about 0.0047 and GT 30 of about 0.0020. GT 20 and AC 20 were not evaluable because of their poor binding. Roughly the aptamers can be divided into three families (FIG. 2); first family: GT 100, GT 80 and GT 60; second family: AC 80, GT 40, AC 40 and GT 30; third family: AC 20 and GT 20.

In FIG. 3, the Log concentration-effect curves of PolyT aptamers are summarized. As it can be appreciated, PolyT100 and PolyT80, i.e. the aptamers having sequence $(T)_{100}$ and $(T)_{80}$, respectively, are much more potent than PolyT60.

Discussion

After four cycles of selection only, a huge increase of the percentage of molecules bound to the protein was seen and, at the ninth cycle, corresponding to a yield of 42%, it was not possible to further enrich the pool. However sequence analysis of the selected aptamers did not show evidence for a common consensus motif repeated among them. At a closer glance it was found that a large number of these molecules were GT/C deficient, therefore unlikely to undergo pairing and to fold into G quartets. Probably single stranded DNA molecules, negative and flexible, bind to this positively charged protein best. Even in the presence of significant amounts of sodium and magnesium chloride in the SELEX buffer, the binding between the target and the protein could be still mainly governed by charged interactions.

To confirm the hypothesis of a peculiar "consensus" rationale, the affinity of one of the selected aptamers, CG51, was compared with several AC and GT oligonucleotides. We validated the fact that CG51 has a remarkably high affinity for cathepsin G with a Kd in the nanomolar range, showing that the selection had effectively lead to a pool of efficient binders. The dissociation constants of $(AC)_{30}$, $(GT)_{30}$ and cmpCG51 that have the same length (and overall structural characteristics) of CG51 were comparable, while shorter molecules showed lower affinity. Double stranded CG51 showed a lower affinity for cathepsin G: this is very interesting considering that it was proven that chromosomal DNA with an average length of 30 bp is able to bind to this protein.

We demonstrated that a linear and flexible single stranded DNA chain, with a length of at least 60, preferably more than 70-80, is more effective in binding cathepsin G than the chromosomal counterpart and also more effective than shorter DNA chains.

The invention claimed is:

1. A method for the treatment of a disease selected from the group consisting of inflammatory occurrences, procoagulant conditions, genetic diseases, degenerative diseases, DNA damages, neoplasia and skin diseases, which comprises administering to a patient in need thereof cathepsin G-inhibiting aptamers consisting of linear DNA or polynucleotide sequences having a chain length of 60-120 nucleotides and undergoing inter and/or intra molecular base pairing to an extent lower than 20%, said sequences being characterized by:

being $(GT)_n$ or $(AC)_n$ oligopolymers in which n is in the range from 30 to 60.

2. The method of claim 1, wherein said cathepsin G-inhibiting aptamers have a chain length of 70-110 nucleotides.

3. The method of claim 1, wherein said cathepsin G-inhibiting aptamers have a chain length of 80-100 nucleotides.

4. The method of claim 1, wherein said cathepsin G-inhibiting aptamers are single stranded sequences.

5. The method of claim 1, wherein said cathepsin G-inhibiting aptamers have a molar content in guanine of 25-50%.

6. The method of claim 1, wherein said cathepsin G-inhibiting aptamers have a molar content in guanine of 35-45%.

7. The method of claim 1, wherein said cathepsin G-inhibiting aptamers are $(GT)_n$ or $(AC)_n$ oligopolymers in which n is in the range from 35 to 60.

8. The method of claim 1, wherein said cathepsin G-inhibiting aptamers undergo inter and/or intra molecular base pairing to an extent lower than 10%.

9. The method of claim 1, wherein said cathepsin G-inhibiting aptamers undergo inter and/or intra molecular base pairing to an extent lower than 5%.

10. The method of claim 1, wherein said disease is an inflammatory disease.

11. The method of claim 7, wherein said cathepsin G-inhibiting aptamers are $(GT)_n$ or $(AC)_n$ oligopolymers in which n is in the range from 40 to 50.

* * * * *

SEQUENCE LISTING

<160> NUMBER OF SEQ ID NOS: 22

<210> SEQ ID NO 1
<211> LENGTH: 60
<212> TYPE: DNA
<213> ORGANISM: unknown
<220> FEATURE:
<223> OTHER INFORMATION: chemically synthesized

<400> SEQUENCE: 1
gggtggcccc ctagtcgcgc actggaagcg gtagtgtcgt gagattcgta tctggggtat      60

<210> SEQ ID NO 2
<211> LENGTH: 60
<212> TYPE: DNA
<213> ORGANISM: unknown
<220> FEATURE:
<223> OTHER INFORMATION: chemically synthesized

<400> SEQUENCE: 2
caacgagtca gggcgtgatt ggtgaagatg tgtggtttgg ccagaaaggg cgatggtgga      60

<210> SEQ ID NO 3
<211> LENGTH: 58
<212> TYPE: DNA
<213> ORGANISM: unknown
<220> FEATURE:
<223> OTHER INFORMATION: chemically synthesized

<400> SEQUENCE: 3
agagctgaga cggacatgct gcccatggag actgttcgag agggtgagcg ggagtggg        58

<210> SEQ ID NO 4
<211> LENGTH: 60
<212> TYPE: DNA
<213> ORGANISM: unknown
<220> FEATURE:
<223> OTHER INFORMATION: chemically synthesized

<400> SEQUENCE: 4
acccctaggt cagcacgtag tgtagggcga tgtgttcatg gcgggaatgt gagttgtggg      60

<210> SEQ ID NO 5
<211> LENGTH: 59
<212> TYPE: DNA
<213> ORGANISM: unknown
<220> FEATURE:
<223> OTHER INFORMATION: chemically synthesized

<400> SEQUENCE: 5
gggcggctcg cgttgtggaa cattcgtggt gccaatgcgt accaggatt gcctcctgt    59

<210> SEQ ID NO 6
<211> LENGTH: 60
<212> TYPE: DNA
<213> ORGANISM: unknown
<220> FEATURE:
<223> OTHER INFORMATION: chemically synthesized

<400> SEQUENCE: 6
gggcgattgg cgaatgcaag ggtaaggttg ggcgattgat gtgcacgtag cgcagagcat    60

<210> SEQ ID NO 7
<211> LENGTH: 55
<212> TYPE: DNA
<213> ORGANISM: unknown
<220> FEATURE:
<223> OTHER INFORMATION: chemically synthesized

<400> SEQUENCE: 7
ggaacgtggt aggtgtgtct gctgtgtgtg gctcgggcag gttgtcaggg tgttt    55

<210> SEQ ID NO 8
<211> LENGTH: 59
<212> TYPE: DNA
<213> ORGANISM: unknown
<220> FEATURE:
<223> OTHER INFORMATION: chemically synthesized

<400> SEQUENCE: 8
gggcatnggg cgtcgtagcc tgaaggtgtg attcgtgcgt tagatggggg gcagtctgc    59

<210> SEQ ID NO 9
<211> LENGTH: 59
<212> TYPE: DNA
<213> ORGANISM: unknown
<220> FEATURE:
<223> OTHER INFORMATION: chemically synthesized

<400> SEQUENCE: 9
cggtggagag gtcgcaatga cacggttgac gataggcccc ttgctaacat cggttggtg    59

<210> SEQ ID NO 10
<211> LENGTH: 60
<212> TYPE: DNA
<213> ORGANISM: unknown
<220> FEATURE:
<223> OTHER INFORMATION: chemically synthesized

<400> SEQUENCE: 10
caacgtgtga tatgtgggta tacgcttggg tgttacgctg agcacagagg gtattcgtgt    60

<210> SEQ ID NO 11
<211> LENGTH: 60
<212> TYPE: DNA
<213> ORGANISM: unknown
<220> FEATURE:
<223> OTHER INFORMATION: chemically synthesized -continued

<400> SEQUENCE: 11
agsgggcagc agcacaccac acatgtacgt gggggattgc attgtgtact tagacggtat    60

<210> SEQ ID NO 12
<211> LENGTH: 60
<212> TYPE: DNA
<213> ORGANISM: unknown
<220> FEATURE:
<223> OTHER INFORMATION: chemically synthesized

<400> SEQUENCE: 12
ggcctgggtg atgtactatg tatgcgtcgt ggtggctggt aaaggggtc tgctatgggt    60

<210> SEQ ID NO 13
<211> LENGTH: 60
<212> TYPE: DNA
<213> ORGANISM: unknown
<220> FEATURE:
<223> OTHER INFORMATION: chemically synthesized

<400> SEQUENCE: 13
ccacggacgc tgtgagcggc caacggatgg gaatcacgat ctggcccgaa ccacataccg    60

<210> SEQ ID NO 14
<211> LENGTH: 56
<212> TYPE: DNA
<213> ORGANISM: unknown
<220> FEATURE:
<223> OTHER INFORMATION: chemically synthesized

<400> SEQUENCE: 14
tcacactagg gcacttgcta agtagctatg taactcgatc atacttatta ggcttg        56

<210> SEQ ID NO 15
<211> LENGTH: 61
<212> TYPE: DNA
<213> ORGANISM: unknown
<220> FEATURE:
<223> OTHER INFORMATION: chemically synthesized

<400> SEQUENCE: 15
aatcgatgga cacttcaacg caacttgaca tggcggtacg tggactcttg tggcgacagt    60
t                                                                    61

<210> SEQ ID NO 16
<211> LENGTH: 60
<212> TYPE: DNA
<213> ORGANISM: unknown
<220> FEATURE:
<223> OTHER INFORMATION: chemically synthesized

<400> SEQUENCE: 16
aacccgtgtg ataaggatat ggtgacttcg tggcacagcg tcgacggact gcccattcca    60

<210> SEQ ID NO 17
<211> LENGTH: 60
<212> TYPE: DNA
<213> ORGANISM: unknown
<220> FEATURE:
<223> OTHER INFORMATION: chemically synthesized

<400> SEQUENCE: 17
ggcgggcggt atgggctgca ggatatgcag gggcgcagag gacagtctgg ccatgtacta    60

```
<210> SEQ ID NO 18
<211> LENGTH: 59
<212> TYPE: DNA
<213> ORGANISM: unknown
<220> FEATURE:
<223> OTHER INFORMATION: chemically synthesized

<400> SEQUENCE: 18
ggcagggacg ttcccaggaa tgcggcacag gcagacagct cccgacgagt accagggtg      59

<210> SEQ ID NO 19
<211> LENGTH: 96
<212> TYPE: DNA
<213> ORGANISM: unknown
<220> FEATURE:
<223> OTHER INFORMATION: chemically synthesized
<220> FEATURE:
<221> NAME/KEY:
<222> LOCATION: (19)...(78)
<223> OTHER INFORMATION: n represents a, t, c, or g

<400> SEQUENCE: 19
cgtacggaat tcgctagcnn nnnnnnnnnn nnnnnnnnnn nnnnnnnnnn nnnnnnnnnn      60
nnnnnnnnnn nnnnnnnngg atccgagctc cacgtg                               96

<210> SEQ ID NO 20
<211> LENGTH: 18
<212> TYPE: DNA
<213> ORGANISM: unknown
<220> FEATURE:
<223> OTHER INFORMATION: chemically synthesized

<400> SEQUENCE: 20
cacgtcgagc tcggatcc                                                   18

<210> SEQ ID NO 21
<211> LENGTH: 15
<212> TYPE: DNA
<213> ORGANISM: unknown
<220> FEATURE:
<223> OTHER INFORMATION: chemically synthesized

<400> SEQUENCE: 21
acgccaagct tgcat                                                      15

<210> SEQ ID NO 22
<211> LENGTH: 18
<212> TYPE: DNA
<213> ORGANISM: unknown
<220> FEATURE:
<223> OTHER INFORMATION: chemically synthesized

<400> SEQUENCE: 22
gggttttccc agtcacga                                                   18
```